United States Patent
Best

(10) Patent No.: US 8,974,365 B2
(45) Date of Patent: Mar. 10, 2015

(54) TREATMENT OF THALAMOCORTICAL DYSRHYTHMIA

(71) Applicant: Steven Richard Devore Best, Deerfield, IL (US)

(72) Inventor: Steven Richard Devore Best, Deerfield, IL (US)

( * ) Notice: Subject to any disclaimer, the term of this patent is extended or adjusted under 35 U.S.C. 154(b) by 0 days.

(21) Appl. No.: 13/826,250

(22) Filed: Mar. 14, 2013

(65) Prior Publication Data
US 2014/0148636 A1  May 29, 2014

Related U.S. Application Data

(60) Provisional application No. 61/729,625, filed on Nov. 25, 2012.

(51) Int. Cl.
| | | |
|---|---|---|
| *A61N 1/36* | (2006.01) | |
| *A61N 2/04* | (2006.01) | |
| *A61M 19/00* | (2006.01) | |
| *A61N 2/00* | (2006.01) | |
| *A61N 2/02* | (2006.01) | |
| *A61M 21/00* | (2006.01) | |

(52) U.S. Cl.
CPC .............. *A61M 19/00* (2013.01); *A61M 21/00* (2013.01); *A61M 2021/0055* (2013.01); *A61N 1/36025* (2013.01); *A61N 2/006* (2013.01); *A61N 2/008* (2013.01); *A61N 2/02* (2013.01)
USPC ......................................................... 600/14

(58) Field of Classification Search
CPC ........... A61N 1/36021; A61N 1/36025; A61N 1/36028; A61N 2/00; A61N 2/002; A61N 2/004; A61N 2/006; A61N 2/008; A61N 2/02; A61N 2/12
USPC .......... 600/9–15; 607/1–3, 45, 46, 48, 58, 61, 607/65, 72–74, 76, 900
See application file for complete search history.

(56) References Cited

U.S. PATENT DOCUMENTS

| | | | | |
|---|---|---|---|---|
| 5,084,007 | A * | 1/1992 | Malin et al. ...................... | 604/20 |
| 6,107,271 | A | 8/2000 | Moskal et al. | |
| 6,176,242 | B1 * | 1/2001 | Rise ............................... | 128/898 |
| 6,591,138 | B1 * | 7/2003 | Fischell et al. .................. | 607/45 |
| 8,492,340 | B2 | 7/2013 | Moskal | |
| 2006/0095088 | A1 * | 5/2006 | De Ridder ....................... | 607/48 |
| 2010/0047342 | A1 * | 2/2010 | Went et al. ..................... | 424/462 |
| 2011/0160223 | A1 * | 6/2011 | Dingledine et al. ...... | 514/253.07 |
| 2011/0178441 | A1 * | 7/2011 | Tyler ............................... | 601/2 |
| 2011/0307029 | A1 * | 12/2011 | Hargrove ......................... | 607/45 |

OTHER PUBLICATIONS

Serrien, D. J., et al., Motor inhibition in patients with Gilles de la Tourette syndrome: functional activation patterns as revealed by EEG coherence. Brain 128, 116-125 (2005).
Spencer, K. M. et al.. Abnormal Neural Synchrony in Schizophrenia., J. Neurosci., 23:7407-7411 (2003).
Spencer, K. M. et al.. Neural synchrony indexes disordered perception and cognition in schizophrenia. Proc. Natl Acad. Sci., 101:17288-17293 (2004).
Raz, A., et al., Firing Patterns and correlations of Spontaneous Discharge of Pallidal Neurons in the Normal and the Tremulous 1-methyl-4-phenyl-1,2,3,6- tetrahydropyridine Vervet Model of Parkinsonism.,J. Neurosci., 20:8559-8571 (2000).
Wichmann, T., et al., The primate subthalamic nucleus. III. Changes in motor behavior and neuronal activity in the internal pallidum induced by subthalamic inactivation in the MPTP model of parkinsonism. J. Neurophysiol. 72:521-530 (1994).
Nini, A., et al., Neurons in the globus pallidus do not show correlated activity in the normal monkey, but phase-locked oscillations appear in the MPTP model of parkinsonism. J. Neurophysiol. 74, 1800-1805 (1995).
Chun-Yen Chen, M.D.,et al.,. Maintenance therapy of celecoxib for major depression with mimicking neuropsychological dysfunction, General Hospital Psychiatry, 1-3 (2010).
Guehl, D. et al.. Tremor-related activity of neurons in the 'motor' thalamus: changes in firing rate and pattern in the MPTP vervet model of parkinsonism. Eur. J. Neurosci., 17:2388-2400 (2003).
Volkmann, J. et al., Central motor loop oscillations in parkinsonian resting tremor revealed by magnetoencephalography, Neurology, 46:1359-1370 (1996).
Llinas, et al., Thalamocortical dysrhythmia: A neurological and neuropsychiatric syndrome characterized by magnetoencephalography. PNAS, 96:15222-15227 (1999).
Zimmerman, M.D., et al., How Should Remission From Depression Be Defined? The Depressed Patient's Perspective, Am J Psychiatry, 163:148-150 (2006).
Benes, M.D., Ph.D., et al., GABAergic Interneurons: Implications for Understanding Schizophrenia and Bipolar Disorder, Neuropsychopharmacology, 25:1-27, No. 1 (2001).
Fuggetta, et al., A neurophysiological insight into the potential link between transcranial magnetic stimulation, thalamocortical dysrhythmia and neuropsychiatric disorders, Experimental Neurology, 1-9 (2012).
Brown SL, et al., The Relationship of Personality to Mood and Anxiety States: a Dimensional Approach, J Psychiatr Res., 26:197-211 (1992).
Leknes S, et al., Relief as a Reward: Hedonic and Neural Responses to Safety from Pain, PLoS ONE 6:1-10 (2011).
Hirschfeld RM, et al., Personality and depression. Empirical findings, Arch Gen Psychiatry, 40:993-8 (1983).

(Continued)

*Primary Examiner* — Charles A Marmor, II
*Assistant Examiner* — Carrie R Dorna
(74) *Attorney, Agent, or Firm* — McDonnell Boehnen Hulbert & Berghoff LLP

(57) ABSTRACT

A method for treating conditions associated with thalamocortical dysrhythmia. The method includes applying transcranial low voltage electrical stimulation (TLVES) therapy or transcranial magnetic stimulation (TMS) therapy to a patient in need thereof, and administering to the patient a dissociative anesthetic during the TLVES therapy or the TMS therapy. A number of conditions including tinnitus, depression and pain can be treated with TLVES or TMS in combination with the dissociative anesthetic, such as an NMADR inhibitor, including ketamine.

21 Claims, No Drawings

(56) References Cited

OTHER PUBLICATIONS

Sterman, et al., Foundation and Practice of Neurofeedback for the Treatment of Epilepsy, Applied Psychophysiology & Biofeedback, 1-17 (2006).
Lehmann, et al., Brain sources of EEG gamma frequency during volitionally meditation-induced, altered states of consciousness, and experience of the self, Psychiatry Research: Neuroimaging, 108:111-121 (2011).
Crawford, et al., The Nature of Hypnotic Analgesia: Neurophysiological Foundation and Evidence, Contemporary Hypnosis, 15:22-33 (1998).
Sawaki, et al., A Common Neural Mechanism for Preventing and Terminating the Allocation of Attention, J. Neurosci., 32:10725-10736 (2012).
Egner, et al., Hypnosis decouples cognitive control from conflict monitoring processes of the frontal lobe, NeuroImage 27:969-978 (2005).
Liu, P., et al., Studies of properties of "Pain Networks" as predictors of targets of stimulation for treatment of pain, Frontiers in Integrative Neuroscience, 5: 1-7 (2011).
Crawford., Brain Dynamics and Hypnosis: Attentional Disattentional Processes, The International Journal of Clinical and Experimental Hypnosis, XLII:204-232 (1994).
Bowirrat, et al., Neuro-psychopharmacogenetics and Neurological Antecedents of Posttraumatic Stress Disorder: Unlocking the Mysteries of Resilience and Vulnerability, Current Neuropharmacology, 8:335-358 (2010).
Akiskal, et al., The distinct temperament profiles of bipolar I, bipolar II and unipolar patients☆, Journal of Affective Disorders, 92:19-33 (2006).
Marek Jarema, Is the patient really the same after a major depressive episode? Medicographia, 31:164-174 (2009).
Lanius, R.A., et al., Recall of emotional states in posttraumatic stress disorder: an fMRI investigation. Biol. Psychiatry, 53:204-210 (2003).
Carol S. Dweck, Can Personality Be Changed? The Role of Beliefs in Personality and Change, Current Directions in Psychological Science, 17:391-394 (2008).
Simon N. Young, PhD., Biologic effects of mindfulness meditation: growing insights into neurobiologic aspects of the prevention of depression, J. Psychiatry Neurosci, 36:75-7 (2011).
Crawford, H., et al., Hypnotic Analgesia: 1. Somatosensory Event-Related Potential Changes to Noxious Stimuli and 2. Transfer Learning to Reduce Chronic Low Back Pain. The International Journal of Clinical and Experimental Hypnosis, XLVI: pp. 92-132 (1998).
Crawford, H., et al., The Nature of Hypnotic Analgesia: Neurophysiological Foundation and Evidence, Contemporary Hypnosis, 15: 22-33 (1998).
Horton, et al., Increased anterior corpus callosum size associated positively with hypnotizability and the ability to control pain, Brain, 127:1741-1747 (2004).
John R. Hughes, Absence seizures: A review of recent reports with new concepts. Epilepsy & Behavior 15:404-412 (2009).
Walter Paulus, Transcranial electrical stimulation (tES—tDCS; tRNS, tACS) methods, Neuropsychological Rehabilitation, 21:602-617 (2011).
Marije aan het Rot, et al., Ketamine for Depression: Where Do We Go from Here? Biol Psychiatry, 72:537-547 (2012).
Müller, M.D., et al., Long-Term Repetitive Transcranial Magnetic Stimulation Increases the Expression of Brain-Derived Neurotrophic Factor and Cholecystokinin mRNA, but not Neuropeptide Tyrosine mRNA in Specific Areas of Rat Brain, Neuropsychopharmacology, 23:205-215 (2000).
Gersner, et al., Long-Term Effects of Repetitive Transcranial Magnetic Stimulation on Markers for Neuroplasticity: Differential Outcomes in Anesthetized and Awake Animals. The Journal of Neuroscience,31: 7521-7526 (2011).
Chang, MD, et al., Long-Term Effects of rTMS on Motor Recovery in Patients After Subacute Stroke, J. Rehabil Med., 42:758-764 (2010).
Rossi S, et al., Prefrontal [correction of Prefontal] cortex in long-term memory: an "interference" approach using magnetic stimulation, Nature Neuroscience, 4:948-52 (2001).
Isserles, et al., Cognitive—emotional reactivation during deep transcranial magnetic stimulation over the prefrontal cortex of depressive patients affects antidepressant outcome, Journal of Affective Disorders, 128:235-242 (2011).
Eisenberger, et al., Why rejection hurts: a common neural alarm system for physical and social pain. Trends in Cognitive Sciences, 8:294-300 (2004).
Kross, et al., Social rejection shares somatosensory representations with physical pain. PNAS, 108:6270-6275 (2011).
Rutherford, et al., Study Design Affects Participant Expectations—A Survey. J Clin Psychopharmacol., 29: 179-181 (2009).
Simon N. Young, PhD. Biologic effects of mindfulness meditation: growing insights into neurobiologic aspects of the prevention of depression. J Psychiatry Neurosci.,36(2):75-7 (2011).
Miller, M.D., et al., Cytokine Targets in the Brain: Impact on Neurotransmitters and neurocircuits, Depression and Anxiety, 1-10 (2013).
Hannestad, et al., Glucose Metabolism in the Insula and Cingulate Is Affected by Systemic Inflammation in Humans. J. Nucl Med., 53:601-607 (2012).
Norbert Müller. Inflammation and the glutamate system in schizophrenia: implications for therapeutic targets and drug development. Expert Opin. Ther. Targets, 12(12):1497-1507 (2008).
Asadabadi, et al., Celecoxib as adjunctive treatment to risperidone in children with autistic disorder: a randomized, double-blind, placebo-controlled trial. Psychopharmacology, 1-9 (2012).
Edward Tobinick, Perispinal etanercept: a new therapeutic paradigm in neurology. Expert Rev. Neurother., 10:985-1002 (2010).
Schnitzler A, et al., Normal and pathological oscillatory communication in the brain, Nat Rev Neurosci., 6:285-96 (2005).
Schulman JJ., et al., Imaging of thalamocortical dysrhythmia in neuropsychiatry, Front Hum Neurosci, 5:69 (2011).
National Institute of Mental Health. The numbers count: Mental disorders in America (available at: www.nimh.nih.gov/health/publications/the-numbers-count-mental-disorders-in-america/index. shtml) accessed on Apr. 3, 2013.
Warden D, et al., STAR*D Project Results: A Comprehensive Review of Findings, Curr. Psychiatry Rep. 9:449-59 (2007).
Institute of Medicine of the National Academies of Science, Report Brief, Jun. 2011 (available at: http://www.iom.edu/~/media/Files/Report%20Files/2011/Relieving-Pain-in-America-A-Blueprint-for-Transforming-Prevention-Care-Education-Research/Pain%20Research%202011%20Report%20Brief.pdf.
McIntyre RS, et al., The Human Cost of Not Achieving Full Remission in Depression, Can J Psychiatry, 49:10S-16S (2004).
O'Reardon JP, et al., Efficacy and safety of transcranial magnetic stimulation in the acute treatment of major depression: A multisite randomized controlled trial. Biol Psychiatry, 62:1208-16 (2007).
Anderson B, et al., Tolerability and safety of high daily doses of repetitive transcranial magnetic stimulation in healthy young men. J ECT, 22:49-53 (2006).
Holtzheimer PE, et al., Accelerated Repetitive Transcranial Magnetic Stimulation for Treatment-Resistant Depression, Depress Anxiety, 27:960-3 (2010).
Preskorn SH., Ketamine: The Hopes and the Hurdles, Biol Psychiatry, 72:522-3 (2012).
Murrough JW, et al., Rapid and longer-term antidepressant effects of repeated ketamine infusions in treatment resistant major depression. Biol Psychiatry [Epub ahead of print] (Jun. 26, 2012).
Sigtermans MJ, et al., Ketamine produces effective and long-term pain relief in patients with Complex Regional Pain Syndrome Type 1, Pain, 145:304-11 (2009).
Gersner R, et al., Long-term effects of repetitive transcranial magnetic stimulation on markers for neuroplasticity: Differential outcomes in anesthetized and awake animals, J Neurosci., 31:7521-6 (2011).
Wang H-Y, et al., Repetitive transcranial magnetic stimulation enhances BDNF—TrkB signaling in both brain and lymphocyte, J Neurosci., 31:11044-54 (2011).

(56) References Cited

OTHER PUBLICATIONS

Cazzoli D, et al., Theta burst stimulation reduces disability during the activities of daily living in spatial neglect, Brain, 1-14 (2012).
Salvadore G., et al., Anterior cingulate desynchronization and functional connectivity with the amygdala during a working memory task predict rapid antidepressant response to ketamine, Neuropsychopharmacology,35:1415-22 (2010).
Thut G., et al., Rhythmic TMS Causes Local Entrainment of Natural Oscillatory Signatures, Current Biology, 21:1176-85 (2011).
Esser SK., et al. Modeling the Effects of Transcranial Magnetic Stimulation on cCortical Circuits., J Neurophysiol. 94:622-39 (2005).
Massimini M, et al., Cortical mechanisms of loss of consciousness: Insight from TMS/EEG studies, Archives Italiennes de Biologie, 150:44-55 (2012).
Johnson JS, et al., Using EEG to explore how rTMS produces its effects on behavior, Brain Topogr; 22:281-93 (2010).
Allen EA, et al.. Transcranial magnetic stimulation elicits coupled neural and hemodynamic consequences, Science, 317:1918-21 (2007).
Briggs F., et al., Emerging views of corticothalamic function, Curr Opin Neurobiol., 18:403-407 (2008).
Carpenter LL, et al., Transcranial magnetic stimulation (TMS) for major depression: A multisite, naturalistic, observational study of acute treatment outcomes in clinical practice, Depression and Anxiety, 29:587-596 (2012).
Allan, CL, Transcranial Magnetic Stimulation in the Management of Mood Disorders, Neuropsychobiology, 64:163-169 (2011).
Cusin C, et al., Somatic therapies for treatment-resistant depression: ECT, TMS, VNS, DBS., Biol Mood Anxiety Disord., 2:14 (2012).
Lisanby SH, et al., Daily left prefrontal repetitive transcranial magnetic stimulation in the acute treatment of major depression: Clinical predictors of outcome in a multisite, randomized controlled clinical trial. Neuropsychopharmacology, 34:522-534 (2009).
Pascual-Leone A, et al., Transcranial magnetic stimulation in cognitive neuroscience—virtual lesion, chronometry, and functional connectivity, Curr Opin Neurobiol, 10:232-7 (2000).
Young, L., et al., Disruption of the right temporoparietal junction with transcranial magnetic stimulation reduces the role of beliefs in moral judgments, Proc Natl Acad Sci., 107:6753-8 (2010).
Snyder AW, et al., Savant-like skills exposed in normal people by suppressing the left fronto-temporal lobe, J. Integrative Neurosci., 2:149-58 (2003).
Brainsway Reports Positive Pivotal Multicenter Major Depression Trial Results, 31 (Apr. 18, 2012).
Fava M, et al., The problem of the placebo response in clinical trials for psychiatric disorders: Culprits, possible remedies, and a novel study design approach, Psychotherapy Psychosomatics, 72:115-27 (2003).
Rutherford BR, et al., A model of placebo response in antidepressant clinical trials, Am J Psychiatry, [Epub ahead of print] 1-11 (Jan. 15, 2013).
Diazgranados N, et al., A randomized add-on trial of an n-methyl-d-aspartate antagonist in treatment-resistant bipolar depression, Arch Gen Psychiatry, 67:793-802 (2010).
Israel JA., Remission in depression: Definition and initial treatment approaches, J Psychopharmacol., 20:5-10 (2006).
Luber, et al., Self-enhancement processing in the default network: a single-pulse TMS study, Exp Brain Res., 223:177-187 (2012).
S. Murray Sherman, Thalamocortical Loops and Information Processing. Encyclopedia of Pain, 2427-2431 (2007).
D. Jeanmonod, et al., Neuropsychiatric thalamocortical dysrhythmia: surgical implications, Thalamus & Related Systems 2:103-113 (2003).
Schulman, et al., Thalamocortical dysrhythmia syndrome: MEG imaging of neuropathic pain, Thalamus & Related Systems, 3:33-39 (2005).
Ferrarelli, M.D.,et. al. Reduced Evoked Gamma Oscillations in the Frontal Cortex in Schizophrenia Patients: A TMS/EEG Study. Am J Psychiatry, 165:996-1005 (2008).
Eggermont, et al., The neuroscience of tinnitus, TRENDS in Neurosciences, 27:676-682 (2004).
Walton, K.D., et al., Abnormal thalamocortical activity in patients with Complex Regional Pain Syndrome (CRPS) Type I, Pain, 150:41-51 (2010).
Timmermann L, et al., The cerebral oscillatory network of parkinsonian resting tremor. Brain, 126(Pt 1):199-212 (2003).
J.H.McAuley, et al., Physiological and pathological tremors and rhythmic central motor control. Brain, 123:1545-1567 (2000).
George K. Kostopoulos. Involvement of the Thalamocortical System in Epileptic Loss of Consciousness. Epilepsia, 42 (Suppl. 3):13-19 (2001).
Milad, M.R., et al., Neurological basis of failure to recall extinction memory in posttraumatic stress disorder. Biol. Psychiatry, 66:1075-82 (2009).
Lanius, et al., A review of neuro-imaging studies in PTSD: Heterogeneity of response to symptom provocation, J. Psychiatric Research., 40:709-729 (2006).
Pollok, et al., The cerebral oscillatory network of volunatary tremor, J Physiol 554:871-878 (2003).
Urbano, et al., Cocain Acute "Binge" Administration Results in Altered Thalamocortical Interactions in Mice, Biol Psychiatry, 66:769-776 (2009).
Silberstein, P. et al., Patterning of globus pallidus local field potentials differs between Parkinson's disease and dystonia, Brain, 126:2597-2608 (2003).
Vitek, J. L., Pathophysiology of dystonia: a neuronal model, Movement Disorders, 17:S49-S62 (2002).
Muller, et al., Schizophrenia as an Inflammation—Mediated Dysbalance of Glutamatergic Neurotransmission. Neurotoxicity Research, 10:131-148 (2006).
Millan, et al., Cognitive dysfunction in psychiatric disorders: characteristics, causes and the quest for improved therapy, Nature Reviews, Drug Discovery, 11:141-168 (2012).
Jobert, et al., Guidelines for the Recording and Evaluation of Pharmaco-EEG Data in Man: The International Pharmaco-EEG Society (IPEG), Neuropsychobiology, 66:201-220 (2012).
Klug, et al., Dysfunctional pain modulation in somatoform pain disorder patients. Eur Arch Psychiatry Clin Neurosci., 261:267-275 (2011).
McCormick., Cortical and Subcortical Generators of Normal and Abnormal Rhythmicity, International Review of Neurobiology, 49:99-114 (2002).
Davis, et al. The brain's emotional foundations of human personality and the Affective Neuroscience Personality Scales, Neuroscience and Biobehavioral Reviews, 35:1946-1958 (2011).
Bersani FS, et al., Deep transcranial magnetic stimulation as a treatment for psychiatric disorders: A comprehensive review, Eur Psychiatry, 28:30-9 (2012).
Di Lazzaro, V., et al., Ketamine increases human motor cortex excitability to transcranial magnetic stimulation, J. Physiol., 547:485-496 (2003).
Takeuchi, N., et al., A Narcoleptic patient exhibiting hallucinations and delusion, Psychiatry and Clinical neurosciences, 54:321-322 (2000).
Badaway, et al., "The peri-ictal state: cortical excitability changes within 24 h of a seizure", Brain 132:1013-1021 (2009).
Berman, RM., et al., "Antidepressant effects of ketamine in depressed patients", Biol. Psychiatry, 47:351-354 (2000).
Barker, AT., et al., "An introduction to the basic principles of magnetic nerve stimulation", J. Clin. Neurophysiol, 8:26-37 (1991).
Gross, M., et al., "Has repetitive transcranial magnetic stimulation (rTMS) treatment for depression improved? A systematic review and meta-analysis comparing the recent vs. the earlier rTMS studies", Acta Psychiatrica Scandinavica, 116:165-173 (2007).
Mayberg, HS., et al., "Deep brain stimulation for treatment-resistant depression", Neuron, 45:651-660 (2005).
Deng, ZD., et al., "Electric field depth-focality tradeoff in transcrancial magnetic stimulation: simulation comparison of 50 coil designs", Brain Stimul., 6:1-13 (2013).

(56) References Cited

OTHER PUBLICATIONS

Diazgranados, N., et al., Rapid resolution of suicidal ideation after a single infusion of an N-methyl-D-aspartate antagonist in patients with treatment-resistant major depressive disorder, J. Clin. Psychiatry, 71:1605-1611 (2010).
Zarate, CA., et al., "A randomized trial of an N-methyl-D-aspartate antagonist in treatment -resistant major depression", Biol. Psychiatry, 74:250-06 (2012).
Zarate, CA., et al., "Replication of ketamine's antidepressant efficacy in bipolar depression: A randomized controlled add-on trial", Biol. Psychiatry, 71:939-946 (2012).
Ibrahim, L., et al.., "Course of improvement in depressive symptoms to a single intravenous infusion of ketamine vs add-on riluzole: Results from a 4-week, double-blind, placebo-controlled study", Neuropsychopharmacology, 37:1526-1533 (2012).
Najjar S, Pearlman DM, Alper K, Najjar A, Devinsky O. Neuroinflammation and psychiatric illness. J Neuroinflam. 2013;10:43.
Kyle AB, Soleimani LL, Murrough JW. Novel glutamatergic drugs for the treatment of mood disorders. Neuropsych Disease and Treatment. 2013;9:1101-1112.
Pizzagalli DA. Frontocingulate dysfunction in depression: Toward biomarkers of treatment response. Neuropsychopharmacol Rev. 2011;36:183-206.
Pankevich DE, Davis M, Altevogt BM. Glutamate related biomarkers in drug development for disorders of the nervous system workshop summary. Institute of Medicine, of the National Academies. 2011.
Breier A, Malhotra AK, Pinals DA, Weisenfeld NI, Pickar D. Association of ketamine-induced psychosis with focal activation of the prefrontal cortex in healthy volunteers. Am J Psychiatry. 1997;154:805-811.
Malhotra AK, Pinals DA, Adler CM, Elman I, Clifton A, Pickar D, Breier A. Ketamine-induced exacerbation of psychotic symptoms and cognitive impairment in neuroleptic-free schizophrenics. Neuropsychopharmacol. 1997;17:141-150.
Santana N, Troyano-Rodriguez E, Mengod G, Celada P, Artigas F. Activation of thalamocortical networks by the N-methyl-D-aspartate receptor antagonist phencyclidine: Reversal by clozapine. Biol Psychiatry. 2011;69:918-927.
Zarate CA, Mathews DC, Furey ML. Human biomarkers of rapid antidepressant effects. Biol Psychiatry. 2013;73:1142-1155.
Salvadore G, Cornwell BR, Colon-Rosario V, Coppola R, Grillon C, Zarate CA, Manji HK. Increased anterior cingulate cortical activity in response to fearful faces: A neurophysiological biomarker that predicts rapid antidepressant response to ketamine. Biol Psychiatry. 2009;65:289-295.
Scheidegger M, Walter M, Lehmann M, et al. Ketamine decreases resting state functional network connectivity in healthy subjects: Implications for antidepressant drug action. PLoS ONE. 2012;7:e44799.
Stahl SM. Psychiatry stress testing: Novel strategy for translational psychopharmacology (a commentary). Neuropsychopharmacology. 2010;35:1413-1414.
Murrough JW, Iosifescu DV, Chang LC, et al. Antidepressant efficacy of ketamine in treatment-resistant major depression: A two-site randomized controlled trial. Am J Psychiatry. 2013;170:1134-1142.
Katalinic N, Lai R, Somogyi A, Mitchell PB, Glue P, Loo CK. Ketamine as a new treatment for depression: A review of its efficacy and adverse effects. Am N Z J Psychiatry. 2013;47:691-692.
Buckner RL, Andrews-Hanna JR, Schacter DL. The brain's default network anatomy, function, and relevance to disease. Annals of the New York Academy of Sciences. 2008;1124:1-38.
Miyasaka M, Domino EF. Neuronal mechanisms of ketamine-induced anesthesia. Int J Neuropharmacol. 1968;7:557-573.
Fingelkurts AA, Fingelkurts AA, Rytsala H, Suominen K, Isometsa E, Kahkonen S. Composition of brain oscillations in ongoing EEG during major depression disorder. Neurosci Res. 2006;56:133-144.
Victor JD, Drover JD, Conte MM, Schiff, ND. Mean-field modeling of thalamocortical dynamics and a model-driven approach to EEG analysis. PNAS. 2011;108:15631-15638.

Corssen G, Miyasaka M, Domino EF. Changing concepts in pain control during surgery: Dissociative anesthesia with CI-581. Anesth Analg. 1968;47:746-759.
Kupfer DJ, Foster GF, Reich L, Thompson KS, Weiss B. EEG sleep changes as predictors in depression. Am J Psychiatry. 1976;133:622-626.
Kupfer DJ, Foster FG, Coble P, McPartland RJ, Ulrich RF. The application of EEG sleep for the differential diagnosis of affective disorders. Am J Psychiatry. 1978;135:69-74.
Giles DE, Kupfer DJ, Rush AJ, Roffwarg HP. Controlled comparison of electrophysiological sleep in families of probands with unipolar depression. Am J Psychiatry. 1998;155:192-199.
Allen, JJB, Urry HL, Hitt SK, Coan JA. The stability of resting frontal electroencephalographic asymmetry in depression. Psychophysiology. 2004;41:269-280.
Plante DT, Winkelman, JW. Sleep disturbance in bipolar disorder: Therapeutic implications. Am J Psychiatry. 2008;165:830-843.
Wirz-Justice A, Benedetti F, Berger M, Lam, RW, Martiny K, Terman M, Wu JC. Chronotherapeutics (light and wake therapy) in affective disorders. Psychol Med. 2005;35:939-944.
Mayberg, HS. Modulating dysfunctional limbic-cortical circuits in depression: Towards development of brain-based algorithms for diagnosis and optimised treatment. BMJ. 2003;65:193-207.
Riemann D, Konig A, Hohagen F, et al. How to preserve the antidepressive effect of sleep deprivation: A comparison of sleep phase advance and sleep phase delay. Eur Arch Psychiatry Clin Neurosci. 1999;249-237.
Paulus, W., Transcranial electrial stimulation (tES-tDCS; tRNS, tACS) methods, Neuropsychological Rehabilitation, Neuropsychological Rehabilitation, 21:602-617 (2011).
Holtzheimer, et al., Neuromodulation for treatment-resistant depression, F1000 Medicine Reports, 22:1-10 (2012).
Loo, et al., Transcranial direct current stimulation for depression: 3-week, randomised, sham-controlled trial, The British Journal of Psychiatry, 200:52-59 (2012).
Catafau AM. Brain SPECT in clinical practice. Part I: perfusion. J Nucl Med 2001; 42:259-271.
Holman BL, Devous MD. Functional brain SPECT: the emergence of a powerful clinical method. J Nucl Med 1992; 33:1888-1904.
Minoshima S, Koepe RA, Frey KA, et al. Anatomical standardization: linear scaling and nonlinear warping of functional brain images. J. Nucl. Med 1994; 35:1528-1537.
Juni JE, Waxman AD, Devous MD, et al. Procedure guidelines for brain perfusion PSECT using 99mTc radiopharmaceuticals 3.0. J Nucl Med Technol 2009; 37:191-195.
Pliszka SR, Glahn DC, Semrud-Clikeman M et al. Neuroimaging of inhibitory control areas in children with attention deficit hyperactivity disorder who were treatment naïve or in long-term treatment. Am J Psychiatry 2006; 163:1052-1060.
Sheehan W, Thurber S. Review of two years of experiences with SPECT among psychiatric patients in a rural hospital setting. J Psychiatr Pract 2008; 14:318-323.
Owen, Adrian M. McMillan, Kathryn M. Laird, Angela R., and Bullmore, Ed. N-back working memory paradigm: A meta-analysis of normative functional neuroimaging studies. Human Brain Mapping 25 (1): 46-59. doi:10.1002/hbm.20131 (2005).
Crown WH, Finkelstein S, Berndt ER, Ling D, Poret AW, Rush AJ, Russell JM (2002): The impact of treatment-resistant depression on health care utilization and costs. J Clin Psych 63: 963-971.
Sackeim HA (2001): The definition and meaning of treatment-resistant depression. J Clin Psych 62: 10-17.
Masellis M, Rector NA, Richter MA. (2003): Quality of life in OCD: differential impact of obsessions, compulsions, and depression comorbidity. Canadian J Psychiatry, 48(2): 72-77.
Chang CC, Yu SC, McQuoid DR, Messer DF, Taylor WD, Singh K, . . . Payne ME (2011): Reduction of dorsolateral prefrontal cortex gray matter in late-life depression. Psychiatry Res. Neuroimaging, 193: 1-6.
Smith R, Chen K, Baxter L, Fort C, Lane RD (2013): Antidepressant effects of sertraline associated with volume increases in dorsolateral prefrontal cortex. J Affect Disord, 146: 414-419.

(56) References Cited

OTHER PUBLICATIONS

Mantovani A, Westin G, Hirsch J, Lisanby SH (2010): Functional magnetic resonance imaging guided transcranial magnetic stimulation in obsessive-compulsive disorder. Biol Psychiatry, 67(7), e39-e40.

Bloch MH, Wasylink S, Landeros-Weisenberger A, Panza KE, Billingslea E, Leckman JF, . . . Pittenger C. (2012): Effects of ketamine in treatment-refractory obsessive-compulsive disorder. Biol Psychiatry, 72(11): 964-970.

Ursu S, Stenger VA, Shear MK, Jones MR, Carter CS (2003): Overactive action monitoring in obsessive-compulsive disorder Evidence from functional magnetic resonance imaging. Psychological Science 14(4): 347-353.

Hayward G, Mehta MA, Harmer C., Spinks TJ, Grasby PM, Goodwin GM (2007): Exploring the physiological effects of double—cone coil TMS over the medial frontal cortex on the anterior cingulate cortex: an H2150 PET study. Eur J Neurosci, 25(7): 2224-2233.

Zarate, CA, et al., "A Randomized trial of N-methyl-D-asparate antagonist in treatment-resistant major depression," Arch Gen Psychiatry, 63:856-865 (2006).

* cited by examiner

TREATMENT OF THALAMOCORTICAL DYSRHYTHMIA

CROSS-REFERENCE TO RELATED APPLICATION

This application claims the benefit of U.S. Provisional Patent Application Ser. No. 61/729,625, filed Nov. 25, 2012, which is incorporated by reference in its entirety.

BACKGROUND

Neurological disorders strike millions of people worldwide. A number of these varied disorders are associated with thalamocortical dysrhythmia, which is generally identified by a set of neurological and psychiatric conditions produced by abnormal oscillatory activity in the major neural circuit that links the brain's thalamus and cortex. Different symptoms are produced depending on where in the brain the rhythm disruption is occurring, but the neuronal mechanisms are the same. The abnormal rhythmicity interferes with normal communication among and between different regions of the brain, and thereby impairs the motor and cognitive skills, and other neurological functions, that are controlled by those regions of the cortex. Among the disorders associated with thalamocortical dysrhythmia are neurogenic pain, Complex Regional Pain Syndrome (CRPS) also known as (RSD), obsessive-compulsive disorder, depression, panic disorder, Parkinson's disease, schizophrenia, rigidity, dystonia, tinnitus, tremor, epilepsy, and major mood disorders.

Many patients do not respond to traditional treatments for these disorders. For instance, STAR-D (Sequenced Treatment Alternatives to Relieve Depression) predicts that only a third of 20 million Americans diagnosed with a major mood disorder achieve full remission, with a significant patient population remaining refractory to pharmacologic interventions, even after attempts at treatment with trials of a variety of anti-depressant medicines. See The Numbers Count: Mental Disorders in America, National Institute of Mental Health (2012). Similarly, a third of the United States population suffers from chronic, non-remitting pain. At least 40% of the population experiences chronic pain when somatic and emotional sequelae are combined. See Institute of Medicine of The National Academies of Science, Report Brief, June 2011.

The application of novel brain stimulation techniques to treat depression, and possibly other neuropsychiatric disorders, is a new and rapidly growing field. These techniques, such as Transcranial Magnetic Stimulation (TMS) and Transcranial Low Voltage Electrical Stimulation (TLVES) (also known as Transcranial Electrical Stimulation (tES)), are emerging as promising approaches because of their relative ease of use, safety and neurobiological effects.

TLVES involves the use of weak electric currents (1-4 mAmps) passed through brain tissue via electrodes placed on the scalp. Effective electrode placement is known for conditions such as: acute pain, prophylaxis against migraine, for depression, and for auditory hallucinations. tES can be delivered in the form of tDCS (direct current stimulation), tACS (alternating current stimulation), or as tRNS (random noise stimulation), which is a purposefully chaotic current flow. With tES, many parameters can be altered including frequency and range of frequency, shape of wave, and offset (of mathematical base of oscillating wave). The stimulation can affect both background electrical state, or sometimes affect oscillatory state, or even alter neuronal firing. It induces lasting changes in neuronal excitability, as evidenced in physiological studies. This is presumably the mechanism by which repeated stimulation can lead to meaningful therapeutic effects, as seen in the clinic-based studies.

Depression has also been treated with Transcranial Magnetic Stimulation (TMS), which was first introduced in 1985 to demonstrate relatively painless activation of the neuronal systems. In recent years, TMS has been applied to investigate the integrity and consequence of an electromagnetic stimulus propogated along the corticoneuronal system. Most recently, commercial TMS systems have been developed to treat Major Depressive Disorder (MDD). For instance, the NEUROSTAR TMS THERAPY® System (Neuronetics, Inc.) is a 37-minute outpatient TMS procedure that is performed under the supervision of a psychiatrist. It does not require anaesthesia or sedation, and patients remain awake and alert during the procedure. The treatment is typically administered daily for about 4-6 weeks.

During NeuroStar TMS Therapy, magnetic field pulses are generated and aimed at the left, prefrontal cortex, which is an area of the brain that has been demonstrated to function abnormally in patients with depression. These TMS magnetic fields are similar in type and strength as those used in magnetic resonance imaging (MRI) machines. The magnetic field pulses pass unimpeded through the hair, skin, and skull and into the brain.

Once inside the brain, the magnetic field pulses are believed to induce an electrical change within the impacted neural network. The amount of electrical potential created is very small, and cannot be felt by the patient, but it can change the activity of the neural tissue and is thought to lead to the release of neurotransmitter chemicals such as serotonin, norepinephrine and dopamine. In addition, regional Cerebral Blood Flow (rCBF) can be directly altered by TMS.

One of the significant drawbacks of TMS is the need for several weeks of rigorously scheduled treatments which equates to a significant human burden in terms of time, money, and hassle, and which often results in poor patient compliance.

Aside from techniques such as TLVES and TMS, there are many pharmaceutical agents currently available for treating neurological disorders. These include, but are not limited to, anticonvulsants, antiepileptics, barbiturates, barbituric acid derivatives, anesthetic agents, tinnitus-treating agents, selective serotonin reuptake inhibitors, antidepressant agents, neuroleptic agents, antihypertensive agents, antipsychotic agents, calcium channel blockers, ACE inhibitors, and beta-blockers, mood stabilizers, and stimulants, and hallucinogens. However, many of such drugs are limited in their effectiveness and by their significant side effects. For example, many of these drugs are known to cause lightheadedness, depression, insomnia, weight change, sexual dysfunction, cognitive dysfunction, weakness, fatigue, hallucinations, and other side-effects that severely limit their use in the clinic.

Recently, there has been interest in the use of NMDA receptor antagonists for treating neuropsychiatric disorders. NDMA inhibitors are a class of psychopharmacologic agents that work to antagonize, or partially inhibit the action of, the N-methyl d-aspartate receptor (NMDAR). They are commonly used as anaesthesia in animals and humans. The state of anaesthesia they induce is referred to as dissociative anaesthesia. Several synthetic opioids also function as NMDAR-antagonists, such as Meperidine, Methadone, Dextropropoxyphene, Tramadol and Ketobemidone. Some NMDA receptor antagonists, including but not limited to ketamine, dextromethorphan, phencyclidine, and nitrous oxide are known for their dissociative, hallucinogenic, and/or euphoriant properties.

One particular NMDA inhibitor, ketamine, has been shown to be effective in treating depression in patients with bipolar disorder who have not responded to anti-depressants. See Preskorn, Biol. Psychiatry (2012) 72:522-23. In persons with major depressive disorder and bipolar depression, it can produce a rapid antidepressant effect, acting within two hours as opposed to the several weeks often needed by typical antidepressants to work. When used alone, ketamine appears to provide four to seven days of relief from suicidality. Ketamine does not, however, appear to provide lasting relief from suicidality or depression.

Accordingly, the inventors have identified a need for treatments of conditions associated with thalamocortical dysrhythmia that provide more robust and more consistent improvement. Such treatment should also provide a greater likelihood of lasting successful results. Still further, the treatment should preferably reduce the undesirable consequences of drug therapies.

The foregoing description in this section is not prior art to the claims in this application and is not admitted to be prior art by inclusion in this section.

SUMMARY

In one aspect, the disclosure is directed to a method for treating conditions associated with thalamocortical dysrhythmia in a patient. The method includes applying transcranial low voltage electrical stimulation (TLVES) therapy or transcranial magnetic stimulation (TMS) therapy to the patient, combined with administering to the patient a dissociative anesthetic during the TLVES therapy or the TMS therapy.

In various aspects of the disclosure, the condition associated with thalamocortical dysrhythmia may be tinnitus, pain, including Complex Regional Pain Syndrome or Reflex Sympathetic Dystrophy, and known forms of depression, including bipolar depression.

In another aspect, the dissociative anesthetic is an N-methyl d-aspartate receptor (NMDAR) antagonist, such as ketamine, which can be administered over the course of about 30 to 60 minutes. When the NMDAR antagonist is ketamine, the dose can be about 50-500 mg. Comparable therapeutic doses of other NMDAR antagonists may alternatively be used.

In yet another aspect, the TLVES therapy or TMS therapy is applied prior to, intermittently or consistently during, and after the administration of the NMDAR antagonist. In particular, the method may include a priming treatment applied prior to the application of TMS therapy combined with the dissociative anaesthetic.

Still further, another embodiment of the disclosure includes repeating the method of treatment at intervals of 3-7 days at least five times.

These as well as other aspects and advantages, and alternatives, will become apparent to those of ordinary skill in the art by reading the following detailed description, with reference where appropriate to the accompanying drawings.

DESCRIPTION

Exemplary systems and methods are described herein. It should be understood that the word "exemplary" is used herein to mean "serving as an example, instance, or illustration." Any embodiment or feature described herein as "exemplary" or an "example" is not necessarily to be construed as preferred or advantageous over other embodiments or features. The exemplary embodiments described herein are not meant to be limiting. It will be readily understood that certain aspects of the disclosed systems and methods can be arranged and combined in a wide variety of different configurations, all of which are contemplated herein.

In various aspects, the disclosure is directed to a method of treating a thalamocortical dysrhythmia disorder in a patient. The method includes administrating to the patient a therapeutically effective amount of a dissociative anesthetic in combination with transcranial electrical or electromagnetic stimulation, for example TMS, or transcranial low voltage electrical simulation (TLVES).

Non-limiting examples of the neurological disorder associated with thalamocortical dysrhythmia include: depression, chronic depression, bipolar depression, neurological pain or central pain, complex regional pain syndrome (CRPS) also known as reflex sympathetic dystrophy (RSD), obsessive-compulsive disorder, panic disorder, rigidity, dystonia, tinnitus, tremor, epilepsy, petitmal epilepsy; absence epilepsy, autism, Parkinson's disease; obsessive-compulsive disorder (OCD), schizophrenia, schizoaffective psychosis, migraine, and restless legs syndrome, among others. In addition, users of various substance of abuse, including such as heroin, opiates, cocaine, psychostimulants, alcohol and tranquilizers, are known to have thalamocortical dysrhythmia.

TMS involves creating and applying a fluctuating magnetic field in a controlled manner. The flux created by the expansion and contraction of the magnetic field creates electrical changes in the patient's tissue impacted by the TMS head coil. Sometimes the result is thought to depolarize neurons and to generate action potentials. Another possible result is thought to be alterations in electrical state of the cells affected by magnetic stimulation. One key advantage of TMS over TLVES is that TMS can be delivered to the brain in a more spatially focused way, particularly when a figure-of-eight coil is used. One parameter in TMS treatment as described herein is the electromagnetic frequency used to effect stimulation of the brain tissue. For example, stimulation frequencies at 1 Hz or below may be used in connection with the TMS treatment described herein. TMS treatments at 1 Hz or below have also been called single-pulse TMS, although this term is generally used to describe TMS delivered every few seconds at random intervals. TMS delivered at higher frequency may also be used in connection with the TMS treatment described herein, although such TMS treatment at higher frequency is sometimes described as repetitive TMS (rTMS). The inhibitory and excitatory effects of TMS have been postulated to be akin to long-term potentiation and long-term depression. Another approach is to deliver bursts of stimulation repeatedly, as is the case with theta-burst stimulation (TBS), so that the initial stimulation primes the system for the later stimulation.

Transcranial electrical stimulation administered in low voltages (generally less than about 20 volts) takes several forms, including fixed current DC stimulation (tDCS), alternating current stimulation (tACS), or random (noise) current generation (tRNS). The dose associated with the transcranial low voltage electrical stimulation (TLVES) can be defined with regard to the size and position of the electrodes on the skull and the duration, frequency and intensity (in mAmps) of current. A current of less than about 4 mAmps is commonly used in these techniques. In some embodiments, a commercially available computer controlled DC stimulator may be used.

Although the transcranial electrical and electromagnetic stimulation parameters described herein can be consistent across a relatively broad range of individuals, it should be recognized that there are differences in individual responsiveness to electrical or electromagnetic stimulation for any given individual. One way in which the intensity of the stimulation has typically been calibrated for a given individual is testing the person to derive the minimal intensity of stimulation applied to the motor cortex (often referred to as M1) that evokes a motor response. This motor threshold is generally reported as the minimum intensity required to effectuate stimulation, and may be defined in terms of a percentage of the device's available output or may alternatively be defined in terms of the strength of field measures, i.e., Tesla units. In any event, the degree to which stimulation effects the treatment of a particular patient may be influenced by the stimulation frequency, the treatment repetition frequency (including any pretreatment as described below), and the personal response characteristics of the particular patient. These and similar individual variabilities in response seem to attributable to individual physiology and chemistry, which may be genetically determined at least in part. Specific TMS parameters include the inter-train interval (time between trains of stimulation), number of trains per session, and duration of the session. The most common discomforts are headaches, scalp pain, nausea, and transient hearing difficulty (participants wear ear plugs to avoid this), and these factors too may affect the manner in which patients respond to the treatment. Thus, it should be understood that practicing the methods of described herein on any patient will require the practitioner to exercise a certain amount of experience and judgment to accommodate the patient's individual sensitivities. For example, when a clinician may recognize in advance that a certain patient appears to be medically or psychologically frail in ways that suggest the patient is not a good candidate for TMS, or when a patient may want to avoid TMS therapy, tES treatment offers an effective alternative approach. tES treatment offers an important clinical benefit for patients who may not be good candidates for TMS treatment. Additionally, tES can be important as an effective transition therapy for patients who are sensitive to the adverse effects of TMS treatment.

NMDA receptor antagonists are a class of dissociative anaesthetics that work to antagonize, or inhibit the action of, the N-methyl d-aspartate receptor (NMDAR). They are used as anesthesia for animals and, less commonly, for humans. The state of anesthesia they induce is referred to as dissociative anesthesia. The NMDA receptor is an ionotropic receptor that allows for the transfer of electrical signals between neurons in the brain and in the spinal column. For electrical signals to pass, the NMDA receptor must be open. To remain open, glutamate and glycine must bind to the NMDA receptor. An NMDA receptor that has glycine and glutamate bound to it and has an open ion channel is called "activated."

Ketamine, ((RS)-2-(2-Chlorophenyl)-2-(methylamino)cyclohexanone), is a drug used in human and veterinary medicine. Ketamine is primarily used for the induction and maintenance of general anesthesia, usually in combination with a sedative. Other uses include sedation in intensive care, analgesia (particularly in emergency medicine), and treatment of bronchospasm. Ketamine has a wide range of effects in humans, including analgesia, anesthesia, hallucinations, elevated blood pressure, and bronchodilation, and it maintains perfusion of the brain and heart tissue.

Ketamine has been shown to be effective in treating depression in patients with bipolar disorder who have not responded to anti-depressants. In particular, it is known to cause relief from suicidality. In persons with major depressive disorder, it produces a rapid antidepressant effect, acting within two hours as opposed to the several weeks taken by typical anti-depressants to work.

Ketamine has also being used as an experimental and controversial treatment for Complex Regional Pain Syndrome (CRPS) also known as Reflex Sympathetic Dystrophy (RSD). CRPS/RSD is a severe chronic pain condition characterized by sensory, autonomic, motor and dystrophic signs and symptoms. The pain in CRPS is continuous, it often worsens over time, and it is usually disproportionate to the severity and duration of the inciting event. In obsessive-compulsive disorder (OCD) patients infused with ketamine, the benefit is rather more limited than the above illnesses. (Pittenger, et al., Biol Psychiatry (2012) 72:964-970.)

Other NMDA receptor antagonists include Adamantanes, Amantadine, Memantine, Rimantadine, Arylcyclohexylamines, Dieticyclidine, Esketamine, Eticyclidine, Gacyclidine, Metaphit, Methoxetamine, Neramexane, Phencyclidine, Phenylhexylcyclopyrrolidine, Rolicyclidine, Tenocyclidine, Tiletamine, Methoxydine (4-MeO-PCP), Morphinans, Dextromethorphan, Dextrorphan, Methorphan, Morphanol, 2-MDP, 8A-PDHQ, Aptiganel, Dexoxadrol, Diethyl ether, Dizocilpine, Etoxadrol, Ibogaine (found in Tabernanthe iboga), Midafotel, NEFA, Nitrous oxide, Noribogaine, Perzinfotel, Remacemide, Selfotel, and Xenon.

In one aspect, the disclosure is directed to a method for treating a condition associated with thalamocortical dysrhythmia. The method includes treating a patient with transcranial electrical or electromagnetic stimulation, for example TMS or TLVES, in combination with a dissociative anesthetic. In one aspect, the dissociative anesthetic is an NMDAR inhibitor, for example, ketamine. Use of electrical or electromagnetic stimulation in combination with the dissociative anesthetic such as ketamine results in an improved therapeutic response, often at a reduced dosage of the dissociative anesthetic, as compared to the dosage that is typically necessary for treatment in the absence of the stimulation. For example, when used in combination with TMS, the dosage for ketamine can be from about 10 mg to about 500 mg delivered in a standard commercial formulation over the course of the TMS treatment. More particularly, the ketamine dose can range from about 20 mg to about 400 mg, particularly about 50 mg to about 350 mg, more particularly about 100 mg to 350 mg, and even more particularly about 200 mg to about 300 mg.

The combination treatment (i.e. stimulation in combination with the anesthetic) can extend from approximately 20 minutes to about 120 minutes at an appropriate dosage level. In particular, the period of stimulation can extend from approximately 20 minutes to about 100 minutes, from about 30 minutes to about 90 minutes, from about 40 minutes to about 100 minutes, or more particularly about 20, 30, 40, 50, 60, 70 80, 90, 110, or 120 minutes. In one specific example, a ketamine dose between about 50 and 350 mg is infused within the course of a TMS treatment extending approximately 20-60 minutes. In addition, longer infusion times can provide for a more gentle delivery of ketamine to the patient, and generally result in a better mood and less side effects.

During the combination treatment, the electrical or electromagnetic stimulation occurs during, and optionally before and/or after, the administration of the anesthetic. For example, the administration of the anesthetic can be preceded by a period of stimulation of approximately 1 to 15 minutes, more particularly approximately 3 to 10 min, or even more particularly in the range of about 5 min. Following this preceding period of stimulation, the administration of the anesthetic can begin, and the stimulation can then continue during the course of the administration. Following the administration of the anesthetic, the stimulation can be continued thereafter for approximately 1 to 15 minutes, more particularly approximately 3 to 10 min, or even more particularly in the range of about 5 min.

During a combination treatment using TMS, the TMS head-coil is directed towards the anterior cingulate region for treatment of a majority of the disorders associated with thalamocortical dysrhythmia. When treating tinnitus, stimulation of the association cortex may be appropriate. As more is learned in the future about which regions of the brain are involved in additional various health conditions, it may become more clear as to which regions of the brain should be the focus of stimulation for treatment of such additional health conditions.

The appropriate dose for the TMS treatment may be approximately 80% to 120% of a patient's motor threshold. As understood by one of skilled in the art, a patient's motor threshold reflects the amount of TMS power output at which a patient's thumb will begin to twitch when the TMS is directed to the relevant region of motor strip. It is relevant to brain stimulation as providing one simple way to operate within established safety parameters. More particularly, the appropriate dose for TMS treatment is approximately 90% to 120%, 100% to 120%, or 105% to 115% of a patient's motor threshold. One particular example, the appropriate dose for the TMS treatment is 110% of a patient's motor threshold. Generally, the frequency of the dose is 1 Hz and stimulation is continuous during the combination treatment described herein.

Similar methods are known to those of skill in the art for establishing the appropriate degree and location of stimulation for TLVES. For example, with TLVES, placement of the electrodes can be anterior-posterior (e.g., at mid-forehead and at the center of the back of the head or Oz). Usually, the patient can be treated for 10-50 minutes at 1,000 to 2,500 mAmps, for example about 15, 25, 25 or 45 minutes at about 1,000, 1,200, 1,300, 1,500, 2,000 or 2,500 mAmps. The stimulation may include an offset of about 800 to about 1200 mAmps, for example about 1000 mAmps. TLVES may be continuous during the combination treatment as described herein. In addition, the TLVES may be started before the infusion of a dissociative anesthetic, for example about 1-15 minutes before the start of the infusion, more particularly, for example, about 1, 2, 5, 10 or 15 minutes before the start of the infusion. The TLVES can also continue for a finite time once the infusion is complete.

The dissociative anesthetic can be delivered to the patient by any traditional delivery method, including intravenously, intramuscularly, orally, intranasaly, and, when appropriate, by inhalation. Depending on the anesthetic, its half-life, delivery method and absorption rate, the time of the stimulation during the combination treatment can be adjusted to ensure that the anesthetic is present in therapeutically effective amounts during the stimulation. When the anesthetic is delivered intravenously, the patient experiences its effects essentially immediately. If the anesthetic is delivered orally, additional time can be added to the stimulation to ensure that the stimulation occurs while the anesthetic is therapeutically effective. The pharmacokinetics of ketamine and other dissociative anesthetics are relatively well studied by others in the art, and the understanding derived from those studies provides an adequate basis for predicting the relationship between the time, method, and amount of drug dosing in order to target the time for the anesthetic to enter the bloodstream and become available for treatment to the patient's tissue.

Prior to the combination treatment, the patient may undergo a priming stimulation treatment of approximately 10 to 80 minutes. For example, when TMS is used in the combination treatment, the TMS head-coil is directed at the left and right dorsilateral prefrontal cortices during the priming treatment for approximately 10 to 40 minutes each. The frequency for the priming TMS treatment can be about 1 Hz for the right prefrontal cortex and about 1 Hz for the left prefrontal cortex. The combination treatment can follow immediately after the completion of the priming TMS treatment, or the combination treatment can follow up to one day after the priming treatment, depending on patient tolerance and compliance. Priming with other forms of electrical or electromagnetic stimulation can also be used depending on patient need and tolerance.

In yet another alternative, a patient may be pretreated with electrical or electromagnetic stimulation for weeks or days prior to the combination treatment. For patients that are pretreated, the priming is not necessary. Accordingly, after a series of pretreatments, the combination treatment can begin, for example, the following day. When the combination treatment uses TMS, the pretreatment usually involves from about three days to two weeks of daily (approximately six out of seven days) TMS treatment using a therapeutic regimen. For example, the pretreatment may involve up to four TMS treatment sessions per day for one-half hour with 45 minutes between treatment sessions. As one example, the pretreatment sessions include stimulation at one Hz directed at the dorsilateral prefrontal cortex (left), stimulation at 10 Hz directed again to the left prefrontal cortex, stimulation at 20 Hz to the right prefrontal cortex, and stimulation at 20 Hz to the region overlaying the anterior cingulate region.

Some patients are apprehensive about treatment with ketamine and may be susceptible to fear. Accordingly, use of anti-anxiety medications such as Valium (diazepam) or Versed (midazolam) are appropriate. In addition, anti-nausea medications, such as Zofran (Ondansetron), may be appropriate for some patients.

Significant positive outcomes have been associated with the combination of TMS treatment plus ketamine when the combination is delivered on a weekly or bi-weekly basis. Other alternatives include, for example, treatment every 2, 3, 4, 5, 6, 8, 9, 10, 11, 12, 13, 15, 16, 17 18, 19, 20, 21 days or more. In some instances, patients abandon therapy for a variety of reasons, but resume after a number of weeks or even months. Positive outcome can be expected after about 2-20, more particular about 5-15 treatments, at regular intervals of about 3-11 days, more particularly about weekly. In addition, positive outcomes have been achieved with longer or shorter intervals, which may be sporadic due to patient scheduling and compliance issues. In particular examples, depression can be successfully treated with at least about 5 treatment sessions, more particularly about 6-8 treatments session, while chronic pain may take several additional treatment sessions to achieve the desired outcome, especially when the pain is accompanied by severe depression and/or addiction. In some instances, a patient may be given ongoing infrequent treatments (e.g., every one to four months) for maintenance purposes.

The use of TMS alone is reported effective in about 20-30% of patients for the treatment of mild to moderate depressions. TMS is reportedly even less effective in treating severe depression. Studies have suggested that the use of ketamine alone in the treatment of depression results in about a 60-70% success rate. However, in order to achieve this success for ketamine alone, the dosages for ketamine are reportedly 5-15 times higher than the dose necessary when ketamine is used in combination with TMS as described herein. In addition, relief with ketamine alone appears to be highly transitory in the ketamine-alone studies.

In comparison, the percentage of patients that completed treatment with a combination of TMS plus ketamine achieved a positive outcome is higher that the success rate reported with either TMS alone or ketamine alone. Moreover, the patients having positive outcomes from treatment with the combination of TMS plus ketamine, as described herein, tended to achieve a more robust, i.e., long lasting, positive result, and did so with reduced adverse side effects. Positive outcomes include return to work, rehabilitating a failing business, return to college, marriage, reconciling a failing relationship, dependable sobriety from substance abuse, and dramatic reductions in destructive doses of opioid narcotics. Moreover, many patients who achieved positive results after receiving the combination therapy described herein had previously failed all other treatments for their conditions. Those treatments included rTMS, VNS, TLVES, ECT, hyperbaric oxygen treatments, medications including ketamine (alone) infusions, and alternative medicine treatments like homeopathy.

Accordingly, the treatment described provides for better outcomes using less anesthetic in combination with TMS or TLVES. Because less anesthetic is necessary, the treatment results in fewer side effects. In addition, the need for less TMS or TLVES results in better patient compliance, which itself contributes to more positive outcomes. Indeed, patients who initially experience relief from the treatment tend to be motivated to receive additional treatments that provide a lasting benefit.

TLVES/ketamine treatment offers clinical benefit for patients who may not be good candidates for TMS/ketamine treatment. In particular, a clinician may recognize in advance that a certain patient is not a good candidate for TMS. For example, a patient may get more benefit by TLVES/ketamine because the patient becomes too fatigued by the potent effect of TMS/ketamine on overall CBF (cerebral blood flow). Or a patient may become agitated and require extraordinary nursing care to stay in position for the lengthy TMS/ketamine session. TLVES/ketamine treatment offers an effective alternative approach. In addition, TLVES/ketamine can be important as an effective transition therapy for patients who are sensitive to the adverse effects of TMS/ketamine treatment. TLVES/ketamine can be less taxing for the less robust people, and thus a good choice for those people once they are already on the path to stable recovery.

In another aspect, the disclosure is directed to a method of preventing side effects associated with the treatment of conditions associated with thalamocortical dysrhythmia with dissociative anesthetics. For example, the side effects can be minimized or prevented by using less anesthetic to treat patients. In this method, the dissociative anesthetic is administered in combination with TMS or TLVES. Similarly, in another aspect, the disclosure is directed to a method of reducing the dose of a dissociative anesthetic for treating a condition associated with thalamocortical dysrhythmia. In these aspects, the dose of the anesthetic can be reduced by about 2-20 times the amount normally administered for treatment of the conditions. In other aspects, the dose can be reduced 5-15 times, more particularly 10-15 times, and even more particularly, about 5, 10 or 15 times. In a particular example where the dissociative anesthetic is ketamine, the dose for treating the condition is from about 20 mg to about 400 mg, about 50 mg to about 350 mg, more particularly about 100 mg to 350 mg, and even more particularly about 200 mg to about 300 mg. In another example where the dissociative anesthetic is ketamine, the dose for treating the condition is from about 0.1-6.0 mg/kg, more particularly about 0.5-5.0 mg/kg, even more particularly, about 1.0-4.0 mg/kg.

EXAMPLES

Example 1

TMS/Ketamine Treatment

Thirty-five patients were treated with a combination of ketamine and TMS. All of the 28 patients that completed treatment identified in Table 1 had a positive outcome with the treatment regimen identified in Table 2 (Tables 1 and 2 appear at the end of specification prior to the claims). For simplicity of presentation in Table 2, patients receiving treatment more than once a week are shown as receiving a single treatment for that week. Also, intervals are rounded to the nearest week.

Some patients received a pretreatment (PT) for 3 days to two weeks of daily (usually 6 or 7 days) TMS treatment (generally indicated on FIG. 2 as "PT days" or "PT weeks"). Others received a priming TMS treatment prior to the combination treatment. Some patients received neither pretreatment nor priming, although most patients received one or the other. Since the priming treatment is less rigorous than several days of pretreatment, all patients receiving pretreatment were ultimately switched to priming or neither. Pretreatment and or priming treatment were administered based upon diagnosis and patient compliance. Patients suffering from chronic pain generally responded better when pretreatment or priming was administered, while the difference in depressed patients was less pronounced.

Based upon lack of success reported in previous studies with the use of ketamine alone, TMS alone, or TLVES alone, the positive outcomes shown in Table 1 suggest the synergistic effect of a combination therapy with ketamine and TMS. Moreover, patients receiving the combination therapy appear to have a lasting result which has not previously been reported with ketamine alone and is achieved at significantly lower doses of ketamine than previously understood.

Example 2

TLVES/Ketamine Treatment

Three patients were previously treated with TMS/ketamine as described above and had significantly improved. However, these patients were more frail and less robust than the other members of the cohort.

The patients were treated with either tACS or tRNS by defining the anode at F3 and the cathode at F8 in relation to net current flow. Electrical stimulation of the electrodes was applied for 20 minutes. Ketamine was started after 5 minutes and infused continuously for 15-50 minutes for a total dose of 0.5-5.0 mg per kg. For tACS, the parameters were 1200 µAmps, no offset or 1200 µAmps with 1000 µAmp offset. For tRNS, the parameters were 1300 or 2000 µAmps with 1000 µAmp offset. With TLVES/ketamine, all three patients have been able to get the same therapeutic benefits as TMS/ketamine with less of the post-treatment fatigue.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

TABLE 1

| ID | Diagnosis | Outcome | Overall Response |
|---|---|---|---|
| B23 | Fibromyalgia, PTSD, mixed connective tissue disease | off pain medicine, calm, more active, experienced severe nausea | excellent |
| B26 | Bipolar Disorder, poly-substance abuse | returned to college, got married | excellent |
| B3 | Unipolar Depression & ADD | entered graduate school, got out of abusive relationship | excellent |
| B6 | Bipolar Depression | entered graduate school, began to date for first time | excellent |
| C11 | Tourette's and secondary depression | off of inappropriate medicines, calm, in school | good |
| D20 | Depression & frontal lobe disorder | depression lifted, apathy lifted, pace of thought improved | excellent |
| D8 | OCD & secondary depression | back to work and active family life | good |
| H2 | Bipolar Depression | returned to home-life and active mothering | good |
| K10 | CRPS & regulatory disorder of childhood | off of opioid narcotics, entered trade school, saved subject's life | excellent |
| M12 | Unipolar Depression & minor epilepsy | did very well, went back to work, then stopped treatment and relapsed | good |
| M19 | Depression & poly-substance abuse | sober, active with family business | excellent |
| M25 | Panic disorder, secondary depression, dormant alcohol abuse | entered graduate school, sober, back to church life | excellent |
| M33 | Bipolar Disorder, poly-substance abuse | calm, still in early stage of treatment | very good |
| N13 | Bipolar Depression & chronic neck and back pain | off of all opioid narcotics, calm, walking well | very good |
| N14 | Unipolar Depression, ADD, alcohol abuse, concussion | calm, repaired broken business & family life, sober | very good |
| N30 | Depression, fibromyalgia, back pain | off opioid narcotics, not depressed, traveling | excellent |
| N7 | Multiple head injuries and depression | off of all opioid narcotics, back to church life | excellent |
| O34 | ADHD, concussion, back pain, substance abuse | did very well, significant other coaxed subject back to substance abuse | excellent |
| Q9 | Bipolar Depression | back to work, repaired broken marriage | excellent |
| R17 | Childhood depression, PTSD, poly-substance abuse | learned to read, entered college, sober | excellent |
| R32 | OCD & secondary depression, poly-substance abuse | sober, calm, back to college | excellent |
| S1 | Generalized anxiety & secondary depression | returned to college, sober | excellent |
| S36 | Depression, panic attacks | did very well, repaired broken marriage and family | excellent |
| T15 | Bipolar Depression | back to church life and active family life | excellent |
| T29 | Bipolar Disorder, dormant poly-substance abuse | entered graduate school, running family business, still sober | excellent |
| W24 | Depression | back to work and active family life | excellent |
| Z27 | Childhood onset bipolar disorder, ADD, RSD | sober, calm, entered college and at work part-time | very good |
| Z4 | Unipolar Depression & ADD | no longer bedridden, left bad marriage | very good |

TABLE 2

| ID | B23 | B26 | B3 | B6 | C11 | D20 | D8 | H2 | K10 | M12 | M19 | M25 | M33 | N13 | N14 |
|---|---|---|---|---|---|---|---|---|---|---|---|---|---|---|---|
| PT days | Y | Y | Y | Y | N | N | Y | Y | Y | Y | Y | Y | N | N | Y |
| PT weeks | Y | Y | Y | Y | N | N | Y | Y | N | Y | Y | Y | N | N | Y |
| Week | | | | | | Dose (mg, Ketamine) | | | | | | | | | |
| 1 | 20 | 25 | 30 | 33 | 25 | 25 | 25 | 25 | 25 | 28 | 45 | 60 | 50 | 25 | 45 |
| 2 | 30 | 35 | 30 | 33 | | | 30 | 35 | | 30 | | | 50 | 50 | 40 |
| 3 | 40 | 40 | 40 | 33 | 50 | | 45 | 45 | | 30 | | 60 | 75 | 70 | 40 |
| 4 | 50 | | 50 | 33 | 75 | | 55 | 60 | 50 | 60 | | | 100 | 110 | 40 |
| 5 | 55 | | 55 | 33 | 100 | 50 | 70 | 55 | 74 | 75 | 45 | | 125 | 125 | |
| 6 | 60 | 60 | 60 | 33 | 150 | 65 | 85 | 65 | | 75 | 45 | | 125 | 175 | 35 |
| 7 | 65 | 75 | 60 | 30 | 200 | 65 | | 75 | 100 | 75 | 45 | 60 | | 200 | 35 |
| 8 | 70 | | 70 | 33 | 250 | 75 | 80 | 85 | 125 | 105 | 45 | 60 | | 225 | 35 |
| 9 | 70 | | 80 | 43 | 275 | | 90 | 95 | 150 | 105 | | 60 | | 250 | 35 |
| 10 | 60 | | 85 | 43 | 275 | 100 | 100 | 105 | | 105 | 45 | 60 | | | |
| 11 | 80 | | 90 | 43 | 300 | | | 120 | | 100 | 45 | 60 | | | 35 |
| 12 | 85 | | 100 | 45 | 310 | 120 | 110 | 135 | | 100 | 45 | 75 | | | 40 |
| 13 | 95 | | | 45 | 300 | 120 | | | | 100 | 45 | 75 | | | 45 |
| 14 | 105 | | 100 | 45 | 310 | | | 150 | | | 60 | 80 | | | |
| 15 | 115 | | | 45 | 310 | | | | | | 60 | 85 | | | 45 |
| 16 | 115 | | | 46 | 310 | 120 | | 175 | 150 | | 70 | 95 | | | 50 |
| 17 | 130 | | | 60 | 330 | | | 190 | 175 | | 75 | 105 | | | 55 |
| 18 | 130 | | | 70 | 290 | | | | | 110 | 85 | 110 | | | 55 |
| 19 | 140 | | | 80 | 240 | 120 | | | | 120 | 95 | 110 | | | 55 |
| 20 | 140 | | | 70 | 240 | | 120 | | 150 | 120 | 105 | 115 | | | |
| 21 | 150 | | | 70 | 240 | 120 | | | 150 | 135 | 110 | 120 | | | |
| 22 | | | | 70 | 240 | 140 | 120 | | 160 | 110 | 120 | 120 | | | |
| 23 | 150 | | | | | 140 | | | 175 | 110 | 125 | 125 | | | |
| 24 | 150 | | | 90 | 240 | | 135 | | 175 | | 130 | 125 | | | 55 |
| 25 | 160 | | | | | 140 | 150 | | 185 | | 140 | 125 | | | |
| 26 | 160 | | | | 240 | 140 | 165 | | 185 | | 150 | 140 | | | 60 |
| 27 | | | | 105 | | | 180 | | 200 | | 160 | 150 | | 250 | |

TABLE 2-continued

|  | c1 | c2 | c3 | c4 | c5 | c6 | c7 | c8 |
|---|---|---|---|---|---|---|---|---|
| 28 |  | 120 | 150 | 220 |  | 150 | 275 |  |
| 29 |  | 135 | 150 | 240 | 170 | 175 | 300 | 50 |
| 30 |  | 150 |  | 200 | 190 |  | 300 | 55 |
| 31 |  |  |  | 210 |  | 170 |  |  |
| 32 | 100 |  |  | 185 | 210 |  |  | 60 |
| 33 |  |  | 150 | 195 | 230 |  |  | 55 |
| 34 | 120 |  |  | 195 |  | 170 |  | 55 |
| 35 |  |  |  | 200 | 230 | 180 |  |  |
| 36 |  |  |  | 200 |  | 170 |  |  |
| 37 |  | 150 |  | 200 | 250 |  |  |  |
| 38 |  | 165 |  | 215 |  | 180 |  |  |
| 39 |  | 160 |  | 200 | 250 |  |  |  |
| 40 |  |  |  | 200 |  |  |  |  |
| 41 |  | 175 |  | 200 | 250 |  |  |  |
| 42 |  |  |  | 210 |  |  |  |  |
| 43 |  |  |  | 215 |  |  |  |  |
| 44 |  |  |  | 215 |  |  |  |  |
| 45 |  | 185 |  | 215 |  | 180 |  | 40 |
| 46 | 75 |  |  |  |  | 190 |  |  |
| 47 | 90 |  |  |  |  | 200 |  | 50 |
| 48 |  |  |  | 215 |  | 215 |  | 55 |
| 49 |  |  |  | 215 |  |  |  |  |
| 50 |  |  |  | 215 |  | 220 |  | 60 |
| 51 |  |  |  | 200 |  | 220 |  | 70 |
| 52 |  |  |  | 200 |  | 235 |  | 65 |
| 53 |  |  |  |  |  |  |  | 65 |
| 54 |  |  |  |  |  |  |  |  |
| 55 |  |  |  |  |  |  |  |  |
| 56 |  |  |  |  |  | 235 |  | 65 |
| 57 |  |  |  |  |  | 240 |  | 75 |
| 58 |  |  |  |  |  |  |  | 85 |
| 59 |  |  |  |  |  |  |  | 80 |
| 60 | 90 |  |  |  |  |  |  | 75 |
| 61 | 120 |  |  |  |  | 240 |  |  |
| 62 |  |  |  |  |  |  |  |  |
| 63 |  |  |  |  |  |  |  |  |
| 64 |  |  |  |  |  |  |  |  |
| 65 |  |  |  |  |  |  |  | 80 |
| 66 |  |  |  |  |  |  |  |  |
| 68 |  |  |  |  |  |  |  | 80 |
| 69 |  |  |  |  |  | 250 |  | 80 |
| 72 |  |  |  |  |  |  |  |  |
| 73 |  |  |  |  |  |  |  |  |
| 75 |  |  |  |  |  |  |  |  |
| 76 |  |  |  |  |  |  |  |  |
| 77 |  |  |  |  |  |  |  |  |
| 78 |  |  |  |  |  |  |  |  |
| 79 |  |  |  |  |  |  |  |  |
| 81 |  |  |  |  |  | 250 |  |  |
| 82 |  |  |  |  |  |  |  |  |

| ID | N30 | N7 | O34 | Q9 | R17 | R32 | S1 | S36 | T15 | T29 | W24 | Z27 | Z34 |
|---|---|---|---|---|---|---|---|---|---|---|---|---|---|
| PT days | Y | N | Y | Y | N | N | Y | Y | Y | Y | N | Y | Y |
| PT weeks | N | N | N | Y | N | N | N | N | Y | N | Y | Y | Y |

| Week | Dose (mg, Ketamine) | | | | | | | | | | | | |
|---|---|---|---|---|---|---|---|---|---|---|---|---|---|
| 1 | 35 | 25 | 25 | 65 | 25 | 25 | 25 | 25 | 25 | 25 | 25 | 30 | 35 |
| 2 | 40 | 50 | 40 |  | 50 | 50 | 35 |  | 40 | 35 |  | 30 |  |
| 3 | 50 | 45 | 50 |  | 75 | 75 | 45 | 30 |  | 50 | 50 | 38 |  |
| 4 | 50 | 45 |  |  | 100 | 100 |  | 40 |  | 60 | 75 | 40 |  |
| 5 | 75 | 45 |  |  | 115 | 125 |  |  |  |  | 100 |  | 35 |
| 6 | 60 | 42 |  |  | 130 | 150 |  | 40 |  | 45 | 120 | 55 |  |
| 7 | 60 | 40 |  |  | 145 |  |  | 50 |  |  | 145 | 55 |  |
| 8 |  | 30 |  |  | 160 | 150 |  |  |  | 60 | 160 | 60 | 35 |
| 9 |  | 30 |  |  | 160 | 175 |  | 55 | 40 | 60 | 180 | 65 |  |
| 10 |  |  |  |  |  | 200 |  | 55 | 50 |  | 180 | 90 | 35 |
| 11 |  |  | 50 | 80 |  | 200 | 35 |  | 50 |  |  | 30 | 35 |
| 12 |  |  | 75 |  |  |  | 50 |  | 55 |  | 200 | 85 |  |
| 13 |  |  | 100 |  |  |  |  | 60 |  |  | 225 | 90 | 35 |
| 14 | 50 |  | 115 | 90 |  |  |  |  |  |  |  | 100 | 35 |
| 15 | 65 |  |  |  |  |  |  | 70 | 60 | 65 |  | 115 | 35 |
| 16 | 55 |  | 130 |  |  |  |  |  | 60 |  | 250 | 120 | 35 |
| 17 | 60 |  | 145 |  |  |  |  |  | 60 |  |  | 130 | 40 |
| 18 | 70 |  | 160 |  |  |  |  |  | 55 |  | 250 | 70 | 40 |
| 19 |  |  |  |  |  |  | 50 | 70 | 55 |  |  | 70 | 50 |
| 20 |  |  |  |  |  |  |  |  | 55 |  |  |  |  |
| 21 |  |  |  |  |  |  | 55 |  | 60 |  | 275 | 85 | 55 |
| 22 |  |  |  | 90 |  |  |  |  |  |  |  | 95 | 65 |

TABLE 2-continued

|  |  |  |  |  |  |  |  |  |
|---|---|---|---|---|---|---|---|---|
| 23 |  | 160 | 105 |  | 40 |  |  | 110 | 75 |
| 24 |  | 185 |  | 65 | 40 | 80 | 300 |  | 80 |
| 25 |  |  |  | 60 |  | 70 |  | 110 | 90 |
| 26 |  | 200 |  |  | 50 | 80 | 300 | 110 | 70 |
| 27 |  | 200 |  | 60 |  |  |  |  | 100 |
| 28 |  | 225 |  |  | 60 |  |  |  | 115 |
| 29 |  | 250 |  |  |  |  |  |  | 125 |
| 30 |  |  |  |  | 60 |  |  |  | 135 |
| 31 |  |  | 105 | 60 |  |  | 325 |  | 150 |
| 32 | 30 |  | 115 |  | 60 |  |  |  | 130 |
| 33 | 40 |  |  |  |  |  |  |  | 140 |
| 34 | 50 |  | 115 |  | 55 |  |  |  | 140 |
| 35 |  |  |  |  | 50 |  |  |  | 150 |
| 36 |  |  |  |  | 70 |  |  |  | 150 |
| 37 |  |  |  |  |  |  |  |  | 165 |
| 38 |  |  | 130 |  |  |  |  |  | 180 |
| 39 |  |  | 130 |  |  |  |  | 80 | 195 |
| 40 |  |  | 130 |  | 70 |  |  | 95 |  |
| 41 |  |  |  |  |  |  |  |  | 150 |
| 42 |  |  |  | 60 |  |  |  |  | 165 |
| 43 |  |  |  |  | 70 |  |  | 95 |  |
| 44 |  |  |  |  |  |  |  | 90 |  |
| 45 |  |  |  | 60 |  |  |  | 90 |  |
| 46 |  |  |  | 60 |  |  |  | 105 |  |
| 47 |  |  |  |  |  |  |  | 95 |  |
| 48 |  |  | 130 |  |  |  |  |  |  |
| 49 |  |  |  | 60 |  |  |  | 95 |  |
| 50 |  |  |  |  |  |  |  | 95 | 165 |
| 51 |  |  |  | 60 |  |  |  | 110 |  |
| 52 |  |  |  |  |  |  |  |  |  |
| 53 |  |  |  | 60 |  |  |  | 120 | 175 |
| 54 |  |  |  |  |  |  |  |  | 190 |
| 55 |  |  |  |  |  |  |  |  | 200 |
| 56 |  |  |  |  |  |  |  | 120 | 200 |
| 57 |  |  |  |  |  |  |  | 120 |  |
| 58 |  |  | 130 |  |  |  |  |  |  |
| 59 |  |  | 130 |  |  | 60 |  |  |  |
| 60 |  |  | 130 |  |  | 60 |  | 130 | 200 |
| 61 |  |  |  |  |  |  |  |  | 220 |
| 62 |  |  |  |  |  |  |  | 140 | 220 |
| 63 |  |  |  |  |  |  |  | 140 | 220 |
| 64 |  |  |  |  |  |  |  | 145 | 220 |
| 65 |  |  |  |  |  |  |  | 150 | 220 |
| 66 |  |  |  |  |  |  |  | 150 | 220 |
| 68 |  |  |  |  |  |  |  |  | 225 |
| 69 |  |  |  |  |  |  |  |  | 250 |
| 72 |  |  |  |  |  |  |  |  | 275 |
| 73 |  |  |  |  |  |  |  |  | 300 |
| 75 |  |  |  |  |  |  |  |  | 300 |
| 76 |  |  |  |  |  |  |  |  | 325 |
| 77 |  |  |  |  |  |  |  |  | 325 |
| 78 |  |  |  |  |  |  |  |  | 325 |
| 79 |  |  |  |  |  |  |  |  | 325 |
| 81 |  |  |  |  |  |  |  |  |  |
| 82 |  |  |  |  |  |  |  |  | 325 |

The invention claimed is:

1. A method for treating a condition associated with thalamocortical dysrhythmia, the method comprising in combination:
  applying, external to the skull, transcranial low voltage electrical stimulation (TLVES) therapy or transcranial magnetic stimulation (TMS) therapy to a patient suffering from a condition associated with thalamocortical dysrhythmia;
  administering to the patient intravenously, intramuscularly, orally, intranasally or by inhalation a dissociative anesthetic during the TLVES therapy or the TMS therapy,
  wherein the dissociative anesthetic is ketamine administered at a dose of about 50 mg to about 500 mg or at a dose of about 0.5 mg/kg to about 5 mg/kg.

2. The method of claim 1, wherein the TLVES or TMS is applied prior to, during and after the ketamine administration.

3. The method of claim 1, further comprising a priming treatment.

4. The method of claim 1 wherein the method is repeated at intervals of 3-7 days.

5. The method of claim 1, wherein the condition associated with a thalamocortical dysrhythmia is tinnitus.

6. The method of claim 1, wherein the condition associated with a thalamocortical dysrhythmia is substance abuse.

7. The method of claim 1, wherein the dose of the NMDAR antagonist ketamine is administered during the application of the TLVES or TMS.

8. A method for treating pain, the method comprising in combination,
  applying, external to the skull, transcranial low voltage electrical stimulation (TLVES) therapy or transcranial magnetic stimulation (TMS) therapy to an individual having pain;
  administering to the individual intravenously, intramuscularly, orally, intranasally or by inhalation an N-methyl d-aspartate receptor (NMDAR) antagonist during the TLVES therapy or the TMS therapy, wherein the NMDAR antagonist is ketamine administered at a dose of about 50 mg to about 500 mg or at a dose of about 0.5 mg/kg to about 5 mg/kg.

9. The method of claim 8, wherein the TLVES or TMS is applied before, during and after the administration of the NMDAR antagonist.

10. The method of claim 8, wherein the ketamine is infused over a time period of between about 30 and 60 minutes.

11. The method of claim 8, further comprising a priming treatment.

12. The method of claim 8, wherein the method is repeated at intervals of 3-7 days at least five times.

13. The method of claim 8, wherein the pain is associated with Complex Regional Pain Syndrome or Reflex Sympathetic Dystrophy.

14. The method of claim 8, wherein the dose of the NMDAR antagonist is administered during the application of the TLVES or TMS.

15. A method for treating depression, comprising in combination:

applying, external to the skull, transcranial low voltage electrical stimulation (TLVES) therapy or transcranial magnetic stimulation (TMS) therapy to a patient suffering from depression;

administering to the patient intravenously, intramuscularly, orally, intranasally or by inhalation an N-methyl d-aspartate receptor (NMDAR) antagonist during the TLVES therapy or the TMS therapy, wherein the NMDAR antagonist is ketamine administered at a dose of about 50 mg to about 500 mg or at a dose of about 0.5 mg/kg to about 5 mg/kg.

16. The method of claim 15, wherein the TLVES or TMS is applied before, during and after the administration of the NMDAR antagonist.

17. The method of claim 15, wherein the ketamine is infused over a time period of between about 30 and 60 minutes.

18. The method of claim 15, further comprising a priming treatment.

19. The method of claim 15, wherein the method is repeated at intervals of 3-7 days at least five times.

20. The method of claim 15, wherein the depression is bipolar depression.

21. The method of claim 15, wherein the dose of the NMDAR antagonist is administered during the application of the TLVES or TMS.

\* \* \* \* \*